(12) United States Patent
Sakaida et al.

(10) Patent No.: US 7,715,521 B2
(45) Date of Patent: May 11, 2010

(54) IMAGING METHOD AND MODALITY FOR MEDICAL APPLICATION

(75) Inventors: Hideyuki Sakaida, Tokyo (JP); Naoki Mochizuki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 190 days.

(21) Appl. No.: 11/782,388

(22) Filed: Jul. 24, 2007

(65) Prior Publication Data
US 2008/0037714 A1 Feb. 14, 2008

(30) Foreign Application Priority Data
Aug. 9, 2006 (JP) ............................. 2006-216740

(51) Int. Cl.
*A61B 6/03* (2006.01)
(52) U.S. Cl. .......................................... 378/8; 378/207
(58) Field of Classification Search ...................... 378/8, 378/16, 207
See application file for complete search history.

(56) References Cited

U.S. PATENT DOCUMENTS 5,514,957 A 5/1996 Tatebayashi

2006/0262896 A1* 11/2006 Nishide et al. ................ 378/15

FOREIGN PATENT DOCUMENTS

JP  2004-290329 A  10/2004
JP  2005-245914 A  9/2005

\* cited by examiner

*Primary Examiner*—Chih-Cheng G Kao
(74) *Attorney, Agent, or Firm*—Sughrue Mion, PLLC

(57) ABSTRACT

A CT scanner pre-scans a patient by radiating rays of a lower amount from one direction to obtain a perspective prescanning image. An operator defines a main scanning area, in which images for medical application are to be captured, with reference to the prescanning image displayed on a monitor screen. A site recognizer analyzes data of the prescanning image to recognize anatomical structures located in the defined main scanning area. Based on the recognized anatomical structures and order data designating a site of inspection, it is judged whether the main scanning area corresponds to the site of inspection designated by the order data. If not, a warning is displayed on the monitor screen. The site recognizer may recognize all anatomical structures contained in the prescanning image, so that a default main scanning area may be defined on the basis of the recognition results and the order data.

18 Claims, 12 Drawing Sheets

IMAGING METHOD AND MODALITY FOR MEDICAL APPLICATION

FIELD OF THE INVENTION

The present invention relates to a method of capturing an image for medical application from a patient by scanning the patient in a main scanning area that is defined based on an image captured by pre-scanning the patient. The present invention relates also to a modality that captures an image for medical application according to the method of the present invention.

BACKGROUND OF THE INVENTION

In medical facilities, such as clinics and hospitals, a variety of modalities like those for CR (computed radiography), CT (computed tomography), MRI (magnetic resonance imaging), PET (positron emission tomography) and ultrasonography, have been widely used for capturing images of anatomical structures from patients. The images captured by these modalities are utilized for medical diagnoses, and play an important role these days.

Doctors in charge of the patients, such as internists and surgeries, forward orders to a radiological department, instructing a body site of inspection and the inspecting directions. So operators of the modalities, e.g. radiologists, capture medical images according the orders. However, the captured medical images do not always correspond to the site designed by the order. Because the position of anatomical structures differ a little between individual patients, it is difficult especially for tomographic modalities, such as CT scanners and MRI scanners, to adjust the imaging or scanning area to the ordered site.

In order to solve the above problem, CT and MRI scanners have been known from U.S. Pat. No. 5,514,957 and JPA 2005-245914, wherein prescanning is carried out in advance to main-scanning, and an anatomical image of a patient captured by the prescanning is displayed on a monitor, so that the operator defines a main scanning area on the displayed prescanning image by use of a cursor or the like. Then an image served for medical purpose is captured from the main scanning area. These prior arts allow the operator to define the main scanning area graphically on the monitor displaying the anatomical image of the patient, so the operator can define the main scanning area precisely while locating the anatomical structures of the patient.

Even with these prior arts that make prescanning, if the operator misreads the order, the main scanning area defined by the operator does not correspond to the body site of inspection as designated by the order. For example, if the operator mistakes that the site of inspection is abdomen while the order designates chest as the site of inspection, the main scanning area defined with reference to the prescanning image can precisely cover the patient abdominal region but does not correspond to the site of inspection.

JPA 2004-290329 discloses a modality that recognizes what sites are captured as a medical image by the CR scanner and judges whether the captured sites correspond to the site ordered to inspect. Because this prior modality makes the judgment on the formal medical image as captured by the main scanning, the operator must carry out the main scanning again if the captured sites do not correspond to the site of inspection. In that case, it takes extra time to retake the formal image again, and the patient is irradiated excessively by the repeated main scanning. Especially in the CT system, the radiological dosage by one cycle of main scanning is so much that the excessive amount of radiation to the patient due to the repeated main scanning is a serious problem.

SUMMARY OF THE INVENTION

In view of the foregoing, a primary object of the present invention is to provide a medical image capturing method and a modality, which prevent misadjusting of the main scanning area to the site of inspection, and avoid unnecessary irradiation of the patient through repeated main scanning.

According to the present invention, an imaging method for capturing images for medical application comprises steps of inputting order data designating an anatomical structure as an object of inspection; prescanning a patient to take at least a prescanning image; defining with reference to the prescanning image a main scanning area in which images for medical application are to be captured; recognizing anatomical structures contained in the prescanning image by analyzing the prescanning image; judging on the basis of the order data and results of the recognizing step whether the defined main scanning area corresponds to the anatomical structure designated by the order data; and warning if the defined main scanning area does not correspond to the anatomical structure designated by the order data.

The recognizing step may be executed after the defining step, to recognize merely those anatomical structures which are located in the defined main scanning area, or before the defining step, to recognize all anatomical structures contained in the prescanning image. On the basis of the order data and the recognition results, an area corresponding to the anatomical structure designated by the order data may be defined to be the main scanning area.

It is preferable to display the prescanning image and information on the anatomical structure designated by the order data on a screen, so that an operator may define the main scanning area on the displayed prescanning image.

Preferably, the prescanning step includes steps of radiating rays from one direction to the patient, detecting rays transmitted through the patient, and obtaining a perspective image of the patient as the prescanning image based on the detected rays.

According to the present invention, a modality for capturing images for medical application comprises a device for inputting order data designating an anatomical structure as an object of inspection; a device for prescanning a patient to take at least a prescanning image; a device for defining with reference to the prescanning image a main scanning area in which images for medical application are to be captured; a device for recognizing anatomical structures contained in the prescanning image by analyzing the prescanning image; a device for judging on the basis of the order data and recognition results of the recognizing device whether the defined main scanning area corresponds to the anatomical structure designated by the order data; and a device for warning if the defined main scanning area does not correspond to the anatomical structure designated by the order data.

According to the present invention, if the defined main scanning area does not correspond to the anatomical structure designated by the order data, a warning is given before the operator actually starts main scanning. Thus, the present invention prevents the trouble that the images captured for medical application do not correspond to the order, and solves the problem caused by repeating main scanning for retaking correct images from the anatomical structure designated by the order data.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
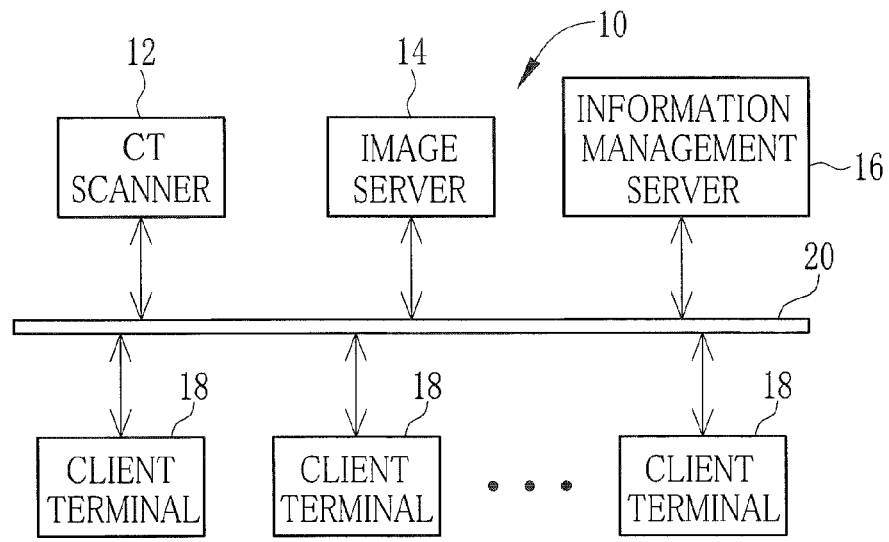
FIG. 1 is a block diagram illustrating a medical graphic information system.

FIG. 1 schematically shows the structure of a medical graphic information system 10 for a medical facility like a hospital. The medical graphic information system 10 is constituted of a modality 12, such as a CT scanner, for capturing images for medical application, like tomographic images, an image server 14 storing a variety of medical images including the tomographic images captured by the CT scanner 12, an information management server 16 for managing various kinds of information used and obtained in the medical facility, and a plurality of client terminals 18 for doctors to utilize for diagnoses and the like. These components are connected to each other through a LAN 20 in the medical facility.

Because the variety of information and medical images obtained in the medical facility are managed as electronic data, the medical graphic information system 10 saves space for storing medical records and photo films of medical images. The medical graphic information system 10 also contributes to improve work efficiency of the medical facility, as it facilitates retrieval of the information and medical images through the respective client terminals 18.

An example of the image server 14 is a server of PACS (picture archiving and communication system for medical application). Besides the tomographic images obtained by the CT scanner 12, the image server 14 stores such medical images that are transferred from other medical facilities through a network or media, and comparative images that are referred to on the diagnosis. The doctors retrieve necessary medical images from the image server 14 through the client terminals 18, to interpret them and use them for informing the patients of the results of diagnoses. Note that the medical images include not only tomographic images captured by the CT scanner 12 but also images captured by other kinds of modalities such as CR scanners and MRI scanners. As the comparative images, illustrations are usable in addition to images captured by the modalities.

An example of the information management server 16 is a server of HIS (hospital information system) or a server of RIS (radiology information system). The information management server 16 manages a variety of information per patient, such as information on the patient, information on medical examination and inspection and accounting information. The information on the patient may include patient's name, patient's ID, patient's address, birthday, age and sex, and medical history and allergies of the patient and family members.

The information on medical examination includes the date of examination of a patient, the medical department in charge of the patient, the name of disorder, the results of diagnosis, duration of therapy, the kinds and amounts of prescribed medicines, and the name of pharmacy in charge of the prescription. The information on inspection includes information on medical images captured from the patient, such as the date of inspection, the machine used for inspection, the applied inspection method and the inspected sites. The information on applied inspection method includes the imaging directions to the patient, such as front imaging and side imaging, and whether a contrast agent is used or not. The accounting information includes information on the charges for examination, medication and inspection, as well as the coverage of insurance.

The client terminals 18 are installed in respective examination booths or in respective examination departments. The doctor enters information through the client terminal 18, for example, while examining the patient. The doctor also uses the client terminal 18 for displaying tomographic images as captured by the CT scanner 12 or the information read out from the information management server 16, to assist the explanation of the diagnostic results. The client terminals 18 may be constituted of well-known personal computers or workstations.

The information management server 16 stores a schedule of reservation for the CT scanner 12. When the doctor is going to get medical images of a patient by the CT scanner 12, the doctor makes an access to the reservation schedule of the information management server 16 through the client terminals 18, and designates the date and time of inspection among available times on the schedule. Then the doctor enters order data specifying the content of inspection to reserve the CT scanner 12. The information management server 16 sends the entered order data to the client terminal 18 installed in the radiology department and the CT scanner 12, each time the information management server 16 accepts a reservation for an inspection or at regular intervals. Based on the order data, the radiologist operates the CT scanner 12 to take tomographic images of the site designated by the order data.

Thus, the information management server 16 manages the information on individual patients and the inspection schedule of the CT scanner 12 so as to avoid double-booking. The order data includes, for example, information on the patient, the doctor, the inspection method and the site of inspection. The information on the doctor includes the name of the doctor who orders the inspection, the belonging department, the phone number and the e-mail address of the doctor, and so forth.

Although many client terminals 18 are installed in the medical graphic information system 10 shown in FIG. 1, it is possible to install only one client terminal. On the other hand, it is possible to install a plurality of CT scanners 12, image servers 14 and information management servers 16.

Figure 2:
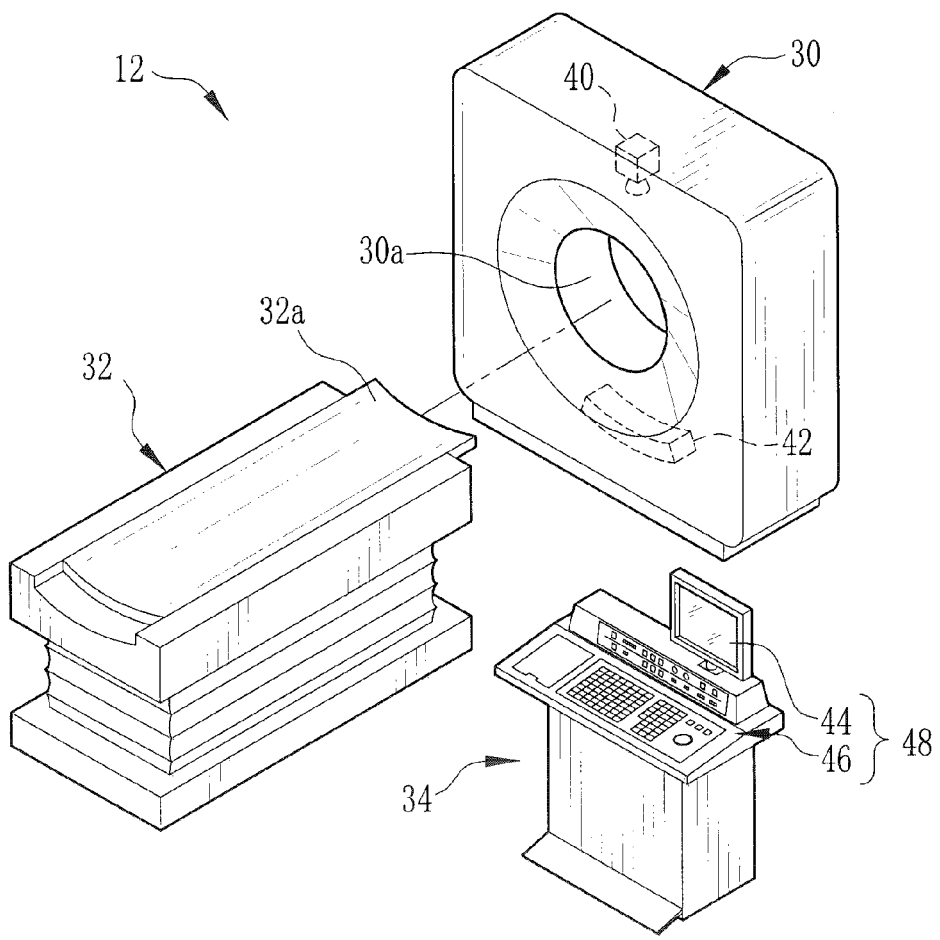
FIG. 2 is a perspective view schematically illustrating an outer appearance of a CT scanner.

FIG. 2 shows an example of the CT scanner 12. The CT scanner 12 consists of a gantry 30 having an X-ray output 40 for irradiating X-rays toward a patient and an X-ray detector 42 for detecting the X-rays transmitted through the patient, a patient couch 32 for carrying the patient into an inspection opening 30a formed in a center of the gantry, and a controller 34 for controlling the gantry 30 and the patient couch 32. Generally, the gantry 30 and the patient couch 32 are installed in a scanning room, whereas the controller 34 is installed in a control room that is separated from the scanning room.

The X-ray output 40 and the X-ray detector 42 are mounted in the gantry 30 so as to be movable along substantially the same circle that is concentric with a round opening 30a of the gantry 30, facing each other across the opening 30a. The gantry 30 drives the X-ray output 40 radiates the X-rays toward the patient laying in the opening 30a, while rotating the X-ray output 40 and the X-ray detector 42 around a center axis of the opening 30a, so as to obtain projection data from many directions.

A schedule 32a to lay the patient thereon is mounted atop the patient couch 32. The patient couch 32 can move the table 32a vertically and horizontally. The lowest position is for the patient to ride on and get off the table 32a with ease. After the patient lies on the table 32a, the height of the table 32a is adjusted to the opening 30a of the gantry 30, and the table 32a is moved horizontally to carry the patient into the opening 30a.

The controller 34 is provided with a console 48 that consists of a monitor 44 and an operating section 46 having a keyboard and various switches. The controller 34 is connected to the gantry 30 and the patient couch 32 through not-shown cables. The controller 34 controls the gantry 30 and 32 according to commands entered by an operator, such as a radiologist, through the operating section 46.

Figure 3:
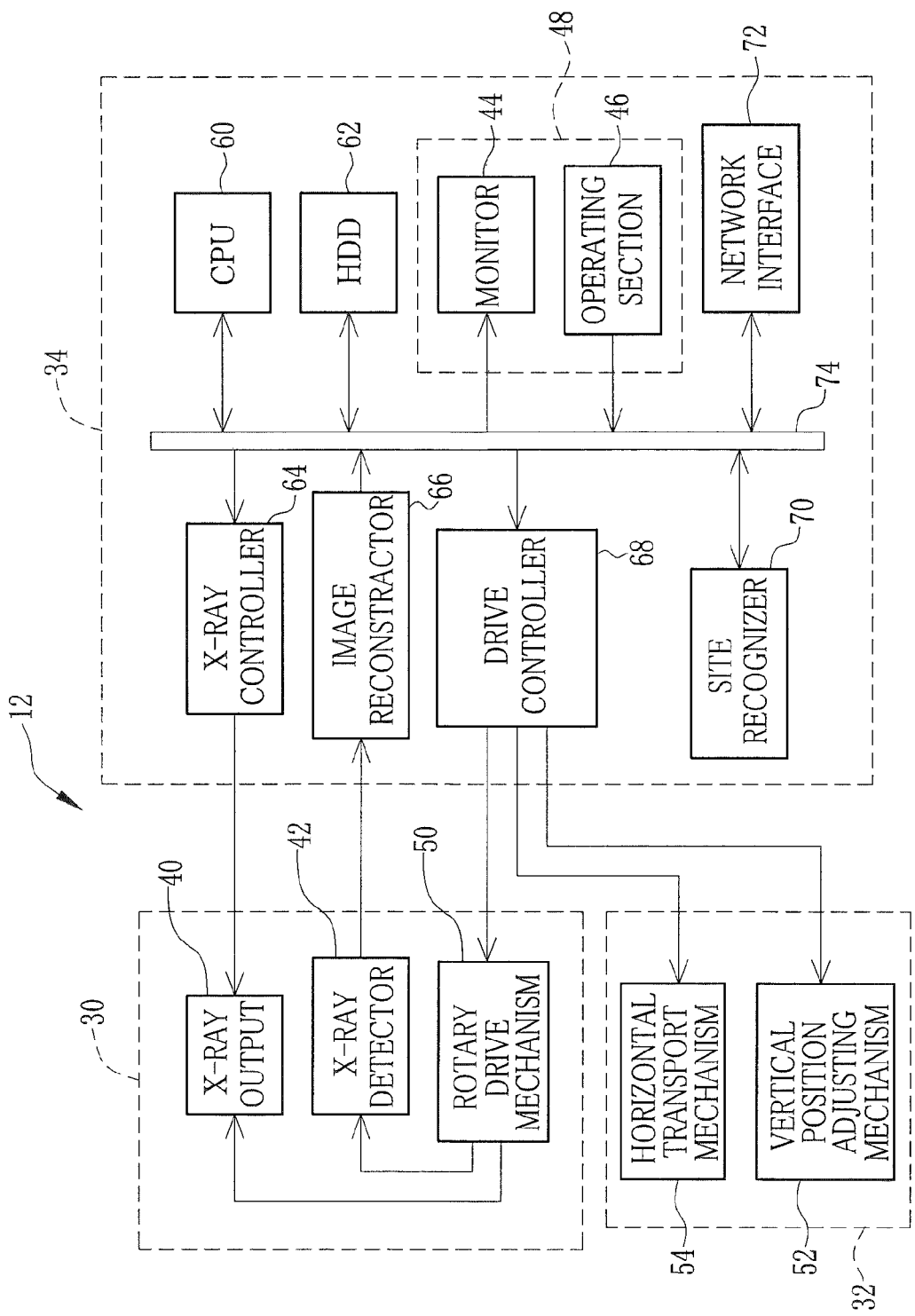
FIG. 3 is a block diagram illustrating an electric construction of the CT scanner.

FIG. 3 shows an electric structure of the CT scanner 12. The gantry 30 is provided with a rotary drive mechanism 50 for rotating the X-ray output 40 and the X-ray detector 42 around the opening 30a. The patient couch 32 is provided with a vertical position adjusting mechanism 52 for adjusting the vertical position of the table 32a, and a horizontal transport mechanism 54 for transporting the table 32a horizontally. These mechanisms 50, 52 and 54 may be well-known mechanisms constituted of motors, gears and so forth.

The controller 34 has the console 48, a CPU 60, a hard disc drive (HDD) 62, an X-ray controller 64, an image reconstructing section 66, a drive controller 68, a site recognizer 70 and a network interface 72. These components are connected to each other through a bus 74. The HDD 62 memorizes various programs for controlling the CT scanner 12. The CPU 60 controls the respective components of the CT scanner 12 according to the programs read from the HDD 62. The CPU 60 executes a variety of processing in response to the commands entered by the operator through the operating section 46, while driving the monitor 44 to display operational screens for the respective programs.

The X-ray controller 64 is connected to the X-ray output 40. Under the control of the CPU 60, the X-ray controller 64 sends control signals to the X-ray output 40, to control the timing and amount of radiation from the X-ray output 40. The image reconstructor 66 is connected to the X-ray detector 42. The image reconstructor 66 reconstructs the projection data of many directions as outputted from the X-ray detector 42, to produce a tomographic image based on the projection data. The image reconstruction may be done according to a known method such as Back Projection method.

The drive controller 68 is connected to the rotary drive mechanism 50, the vertical position adjusting mechanism 52 and the horizontal transport mechanism 54. The drive controller 68 includes not-shown drivers for the respective mechanisms 50, 52 and 54. Under the control of the CPU 60, the drive controller 68 sends drive signals to the mechanisms 50, 52 and 54 to drive them respectively.

The site recognizer 70 analyzes the image produced by the image reconstructor 66, to recognize what sites are contained in the image. For example, the site recognizer 70 analyzes the image by calculating characteristic amounts of the image based on CT values of individual pixels, and compares the calculated characteristic amounts with previously memorized characteristic amounts of respective body sites for matching, wherein the body sites include head, chest, abdomen, pelvic region and limbs.

The network interface 72 connects the controller 34 to the LAN 20. The network interface 72 may be appropriately selected according to the standards of the LAN 20. For example, the network interface 72 is an Ethernet (a registered trademark).

Figure 4:
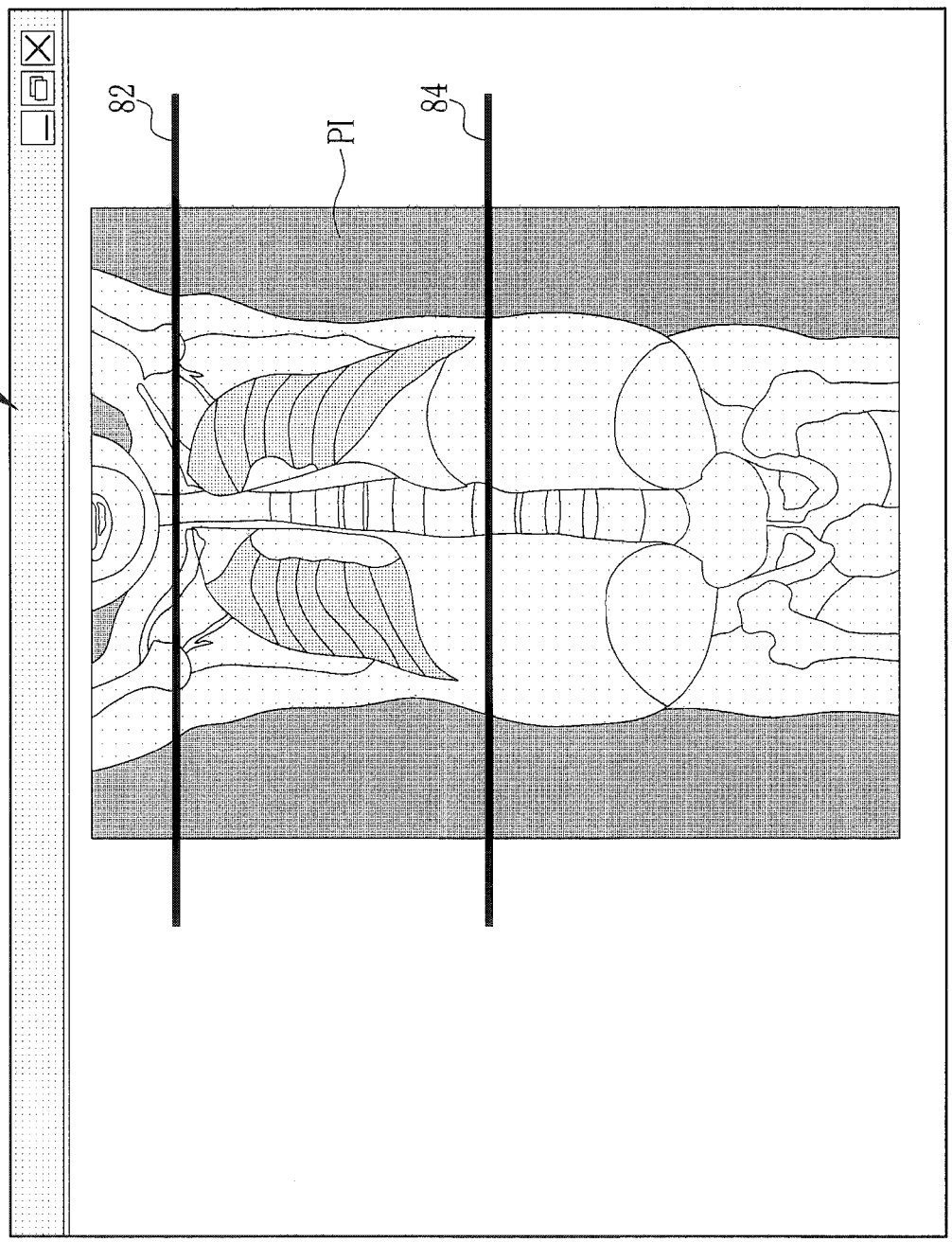
FIG. 4 is an explanatory diagram illustrating an example of a control screen.

The CT scanner 12 makes prescanning in advance to main scanning. The prescanning is for taking a prescanning image that is used for defining an imaging area to take tomographic images by the main scanning. In this embodiment, the prescanning is made by radiating a low amount of X-rays from the X-ray output 40 without rotating the X-ray output 40 and the X-ray detector 42, while transporting the table 32a horizontally at a constant speed. Thereby, a perspective or roentgen image PI as shown for example in FIG. 4 is taken from a single direction of the patient who is laid on the table 32a. The perspective or roentgen image PI taken by the prescanning will be called the prescanning image.

An imaging area for the prescanning may be arbitrary defined by the operator, or all range that can be covered with the gantry 30 and the patient couch 32, i.e. a maximum imaging area taken by the gantry 30 while the table 32a is moved from end to end, is scanned for the prescanning. Hereinafter, an imaging area for the prescanning will be called a prescanning area, whereas an imaging area defined for the main scanning will be called a main scanning area.

The prescanning image PI is displayed on a control screen 80 of the monitor 44, as shown in FIG. 4. The control screen 80 also displays a start line 82 indicating a start position of the main scanning and an end line 84 indicating an end position of the main scanning on the prescanning image PI. While viewing the control screen 80, the operator shifts the start and end lines 82 and 84 up and down by operating the operating section 46 to designate the start and end positions of the main scanning. Thus, the range from the start line 82 to the end line 84 is defined as the main scanning area.

After defining the main scanning area, the operator enters other items, such as slicing thickness, doses the patient with a contrast agent, and makes other necessary operations according to the order data, to start the main scanning. In this way, the operator can define the main scanning area precisely while locating the anatomical structures of the patient with reference to the prescanning image of the patient. Note that other items may be entered at appropriate timing, e.g. before the prescanning, instead of the timing between the prescanning and the main scanning.

Now the operation of the medical graphic information system 10 will be described with reference to the flow chart of FIG. 5.

When a doctor decides it needs to use the CT scanner 12 for diagnosis, he or she makes an access to the reservation schedule of the information management server 16 through the client terminal 18, to reserve the CT scanner 12 by entering order data to a particular time available on the reservation schedule. The information management server 16 sends the entered order data to the client terminal 18 of the radiology department and the CT scanner 12. When the operator confirms the order data on the client terminal 18 or the CT scanner 12, the operator takes images from a patient on the basis of the order data. The order data sent to the CT scanner 12 is fed through the network interface 72 to the HDD 62, to record it in the HDD 62.

The operator of the CT scanner 12 lets the patient be laid on the table 32a of the patient couch 32, and fix the patient with bands or a protector. Then the operator operates the operating section 46 to drive the vertical position adjusting mechanism 52 to adjust the height or vertical position of the table 32a to the opening 30a of the gantry 30. Thereafter, the operator operate the operating section 46 to set up the prescanning area and other conditions and enter a command for starting prescanning to the controller 34. In response to this command, the CPU 60 of the controller 34 controls the gantry 30 and the patient couch 32 to make prescanning, to take the prescanning image PI from the prescanning area.

Thereafter, the CPU 60 drives the monitor 44 to display the taken prescanning image PI and the lines 82 and 84 on the control screen 80. When the operator confirms the completion of prescanning by the displayed prescanning image PI, the operator defines the main scanning area by adjusting the positions of the start and end lines 82 and 84. When the operator completes defining the main scanning area, the CPU 60 sends data of the prescanning image PI and setup data of the main scanning area to the site recognizer 70.

Upon receipt of the prescanning image data and the setup data of the main scanning area, the site recognizer 70 analyzes the prescanning image PI to recognize what site is located in the defined main scanning area. Hereinafter, the site located in the main scanning area will be referred to as main scanning site. The site recognizer 70 sends data on the recognized main scanning site to the CPU 60. The CPU 60 reads out the corresponding order data from the HDD 62, and compares the recognized main scanning site with the site of inspection designated by the order data.

If the CPU 60 judges that the main scanning site corresponds to the site designated by the order data, the CPU 60 starts main scanning in response to a start command from the operator, to take a number of tomographic images from the main scanning area according to the slicing thickness and other setup conditions. The obtained tomographic images are sent through the network interface 72 to the image server 14, and stored as a set of image data per inspection in the image server 14.

Figure 6:
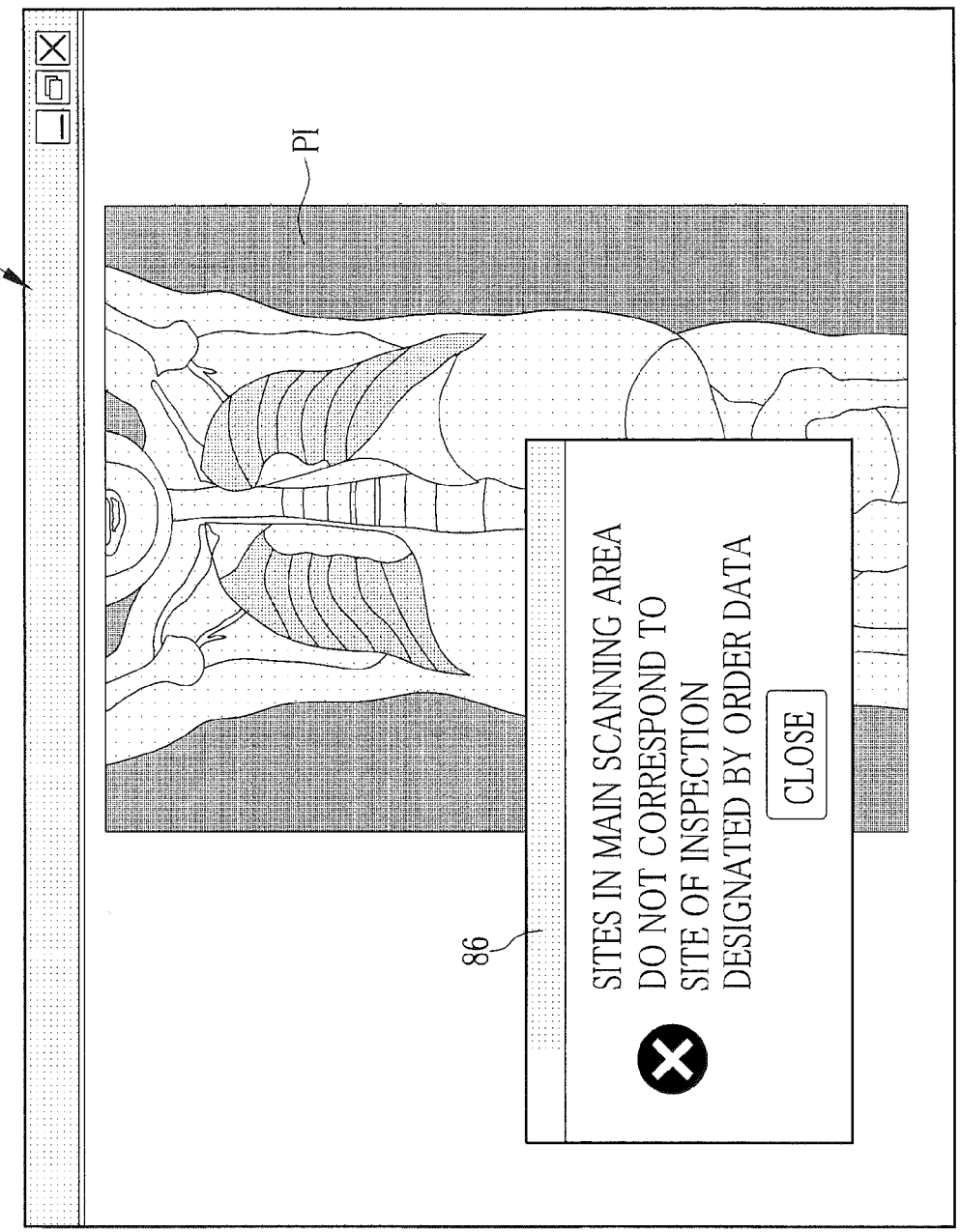
FIG. 6 is an explanatory diagram illustrating an example of a warning popup window displayed on the control screen.

On the other hand, if the CPU 60 judges that the main scanning site does not correspond to the site designated by the order data, the CPU 60 drives the monitor 44 to display a warning popup window 86 on the control screen 80, as shown in FIG. 6, to warn the operator that the defined main scanning area is wrong and must be redefined.

In this way, a warning is displayed automatically when the main scanning site does not correspond to the site designated by the order data, which prevents taking tomographic images of different site from the site designated by the order data. Since the judgment as to whether the site located in the main scanning area corresponds to the site designated by the order data is made as soon as the main scanning area is defined by the operator, i.e. before the main scanning, it is unnecessary to make prescanning or main scanning once again. Thus, the medical graphic information system 10 of the present invention prevents wasteful extension of the inspection time as well as overdosing of the radiation to the patient.

In the above embodiment, the site recognizer 70 recognizes the main scanning site on the basis of the prescanning image PI and the setup data of the main scanning area. But it is possible to extract image data of the main scanning area from the prescanning image PI, and send the extracted image data to the site recognizer 70 for use in recognizing the site in the main scanning area.

Next a second embodiment of the present invention will be described with reference to the flow chart shown in FIG. 7, wherein site recognition is carried out with respect to the whole prescanning image. In the second and following embodiments, equivalent elements to the above described elements will be designated by the same reference numerals, so the details of these elements will be omitted.

Figure 7:
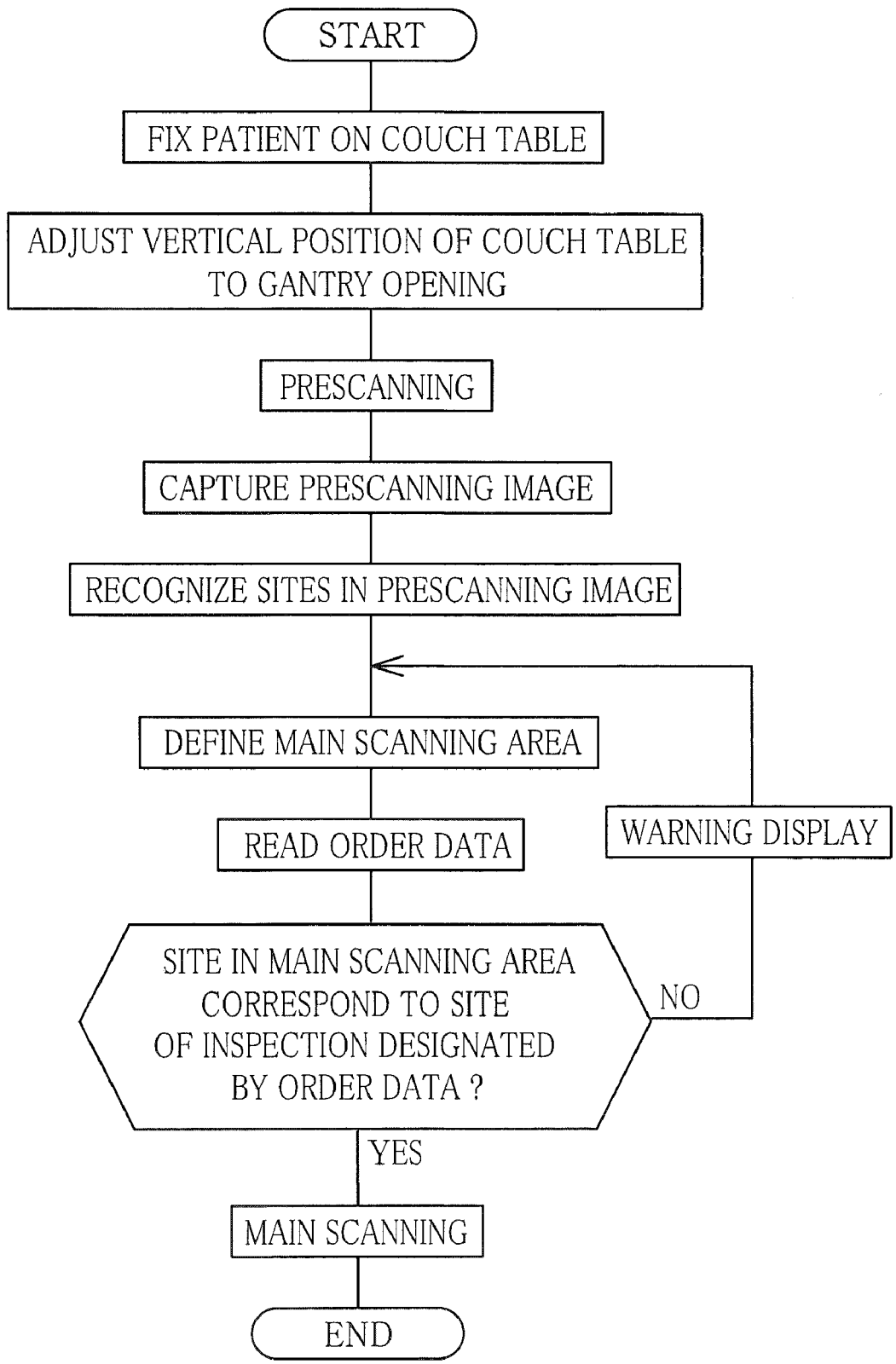
FIG. 7 is a flow chart illustrating a second sequence for capturing images of a patient, wherein site recognition is carried out on a prescanning image before a main scanning area is defined by an operator.
Figure 8:
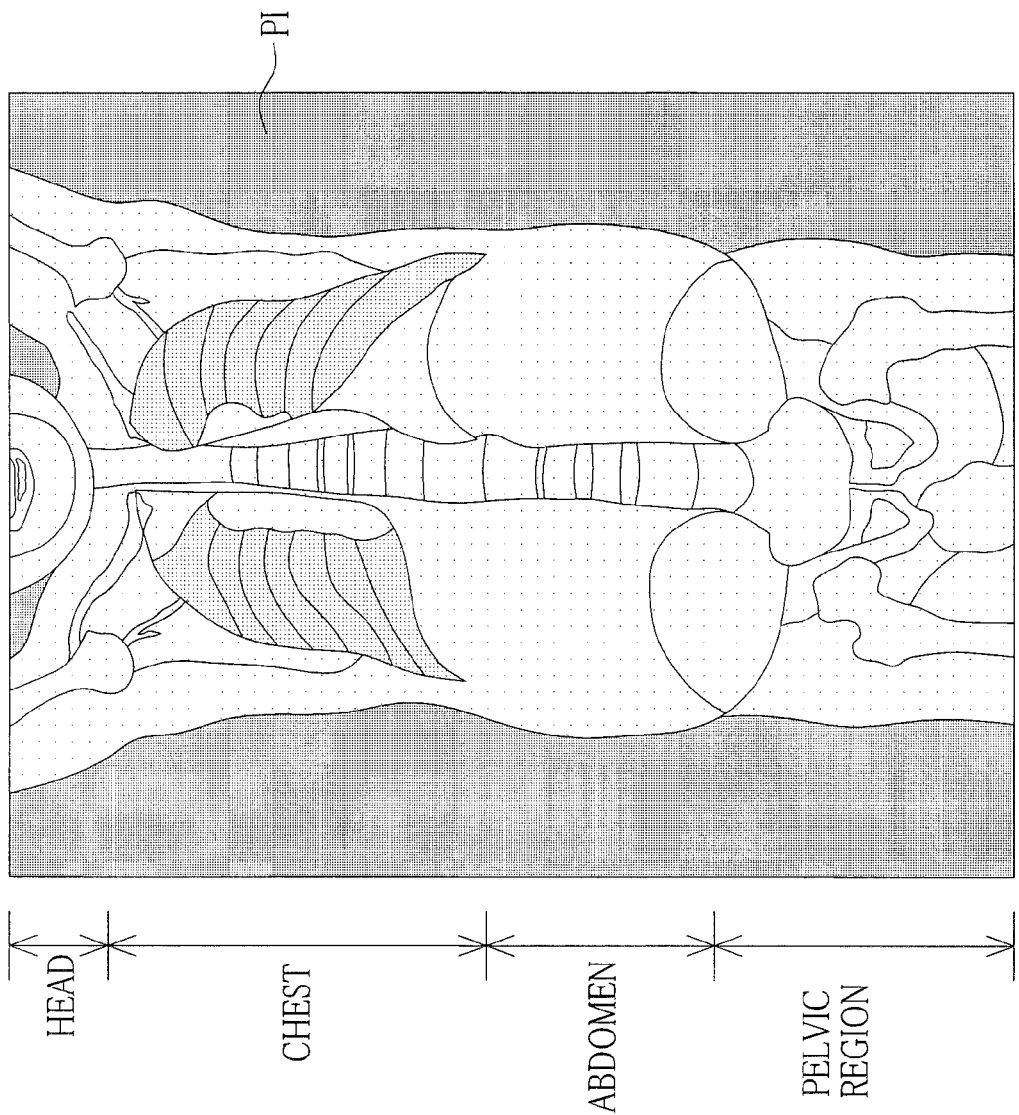
FIG. 8 is a conceptual diagram illustrating the site recognition on the prescanning image.

According to the embodiment shown in FIG. 7, a CPU 60 sends data of a prescanning image PI to a site recognizer 70, so the site recognizer 70 analyzes the image data to recognize respective sites contained in the prescanning image PI, in the way as shown for example in FIG. 8. Then the site recognizer 70 sends the result of site recognition to the CPU 60.

Upon receipt of the site recognition result, the CPU 60 drives a monitor 44 to display the prescanning image PI and start and end lines 82 and 84 in the same way as shown in FIG. 4, to let the operator define a main scanning area with the lines 82 and 84. When the operator completes defining the main scanning area, the CPU 60 reads out the corresponding order data from an HDD 62 and judges based on the order data and the recognition result if the site in the defined main scanning area corresponds to the site designated by the order data.

If the site in the main scanning area corresponds to the site designated by the order data, the CPU 60 starts main scanning. If not, the CPU 60 displays a warning in the same way as shown in FIG. 6, to request the operator for redefining the main scanning area. In this way, the same effect as the first embodiment is achieved by the second embodiment where the site recognition is done before the operator defines the main scanning area.

Figure 9:
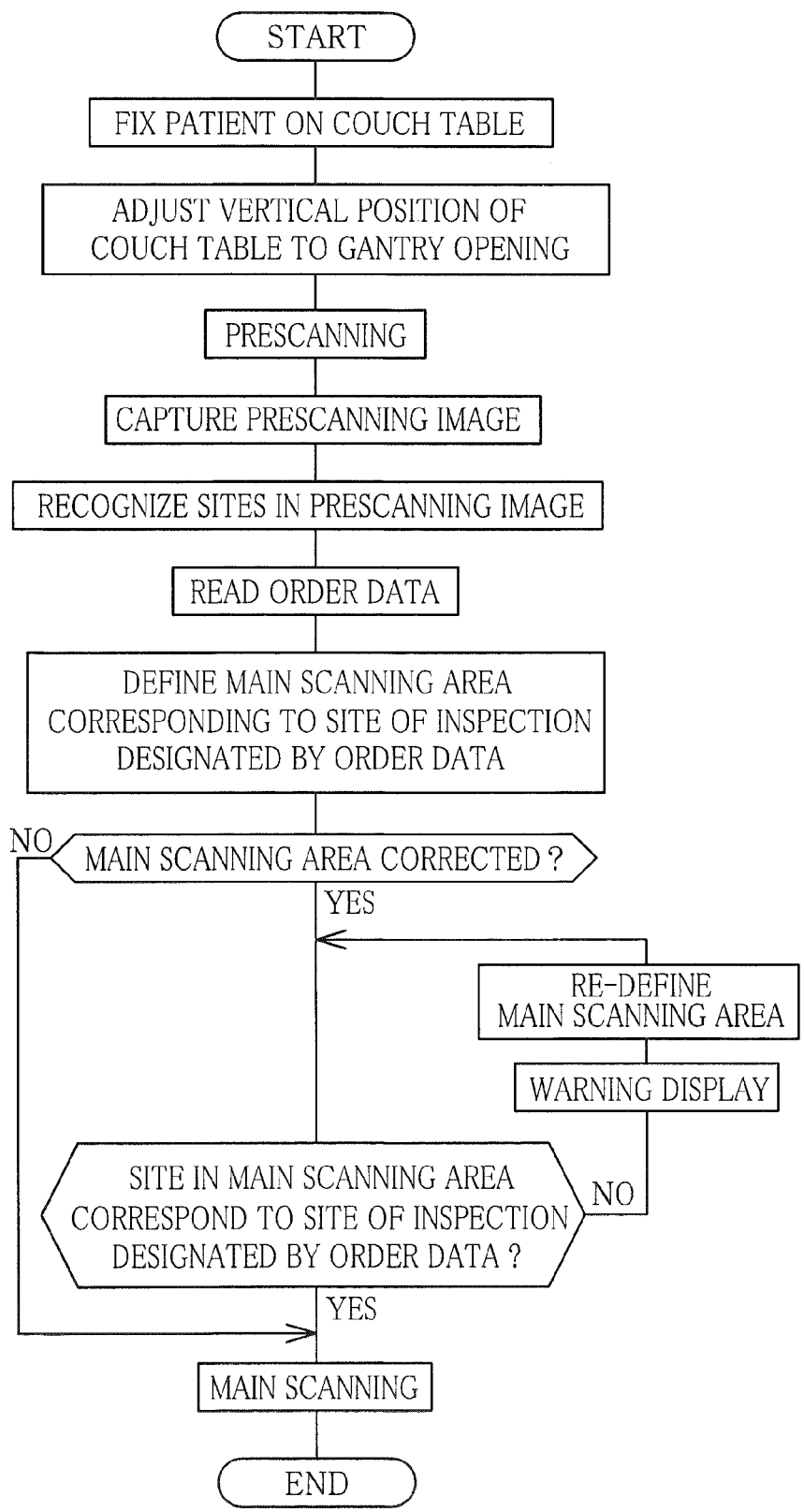
FIG. 9 is a flow chart illustrating a third sequence for capturing images of a patient, wherein a default main scanning area is defined based on the order data and displayed on the control screen for confirmation and manual correction.

FIG. 9 illustrates an imaging method according to a third embodiment, wherein site recognition is carried out with respect to the whole prescanning image, and a main scanning area is automatically defined on the basis of the recognized sites.

Specifically, a CPU 60 sends data of a prescanning image PI to a site recognizer 70, so the site recognizer 70 analyzes the image data to recognize respective sites contained in the prescanning image PI, in the way as shown for example in FIG. 8. Then the site recognizer 70 sends the result of site recognition to the CPU 60.

Upon receipt of the recognition result, the CPU 60 reads out the corresponding order data from an HDD 62 and defines on the basis of the order data and the recognition result a main scanning area corresponding to the site of inspection designated by the order data. After defining the main scanning area, the CPU 60 drives a monitor 44 to display start and end lines 82 and 84 on the prescanning image PI, showing the defined main scanning area. If, for example, the order data designates chest as the site of inspection, the lines 82 and 84 are displayed on a control screen 80 in the way as shown in FIG. 4.

Like the above embodiments, the operator can shift the lines 82 and 84 on the control screen 80 by operating an operating section 46, so the operator can make fine-adjustment of the line 82 or 84 or expand or restrict the main scanning area. When the CPU 60 detects that the operator corrects the main scanning area, the CPU 60 checks if the corrected main scanning area covers the site of inspection designated by the order data. If not, the CPU 60 displays a warning as shown in FIG. 6. If the corrected main scanning area or the main scanning area defined automatically is approved, the CPU 60 starts main scanning across the main scanning area.

Since the main scanning area is automatically defined corresponding to the site designated by the order data, the third embodiment ensures the preventive effect against the error of capturing tomographic images of different site from ones designated by the order data.

Figure 10:
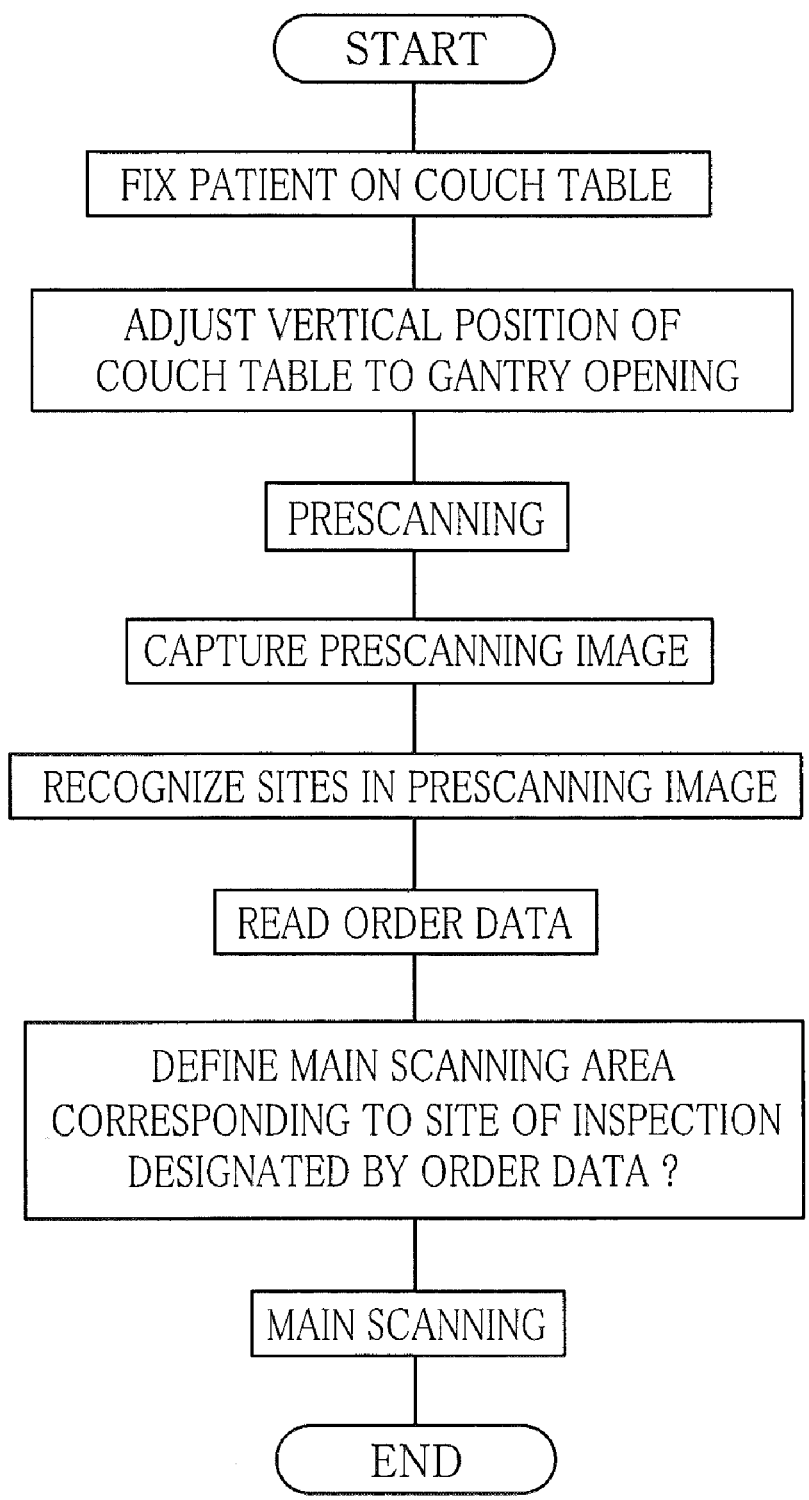
FIG. 10 is a flow chart illustrating a fourth sequence for capturing images of a patient, wherein main scanning is carried out in a default main scanning area defined based on the order data.

It is not always necessary to provide the step of correcting the main scanning area by the operator. In that case, as shown by the flow chart of FIG. 10, the main scanning starts immediately after a main scanning area is defined on the basis of the results of site recognition in a prescanning image PI and corresponding order data read out from an HDD 62.

Figure 11:
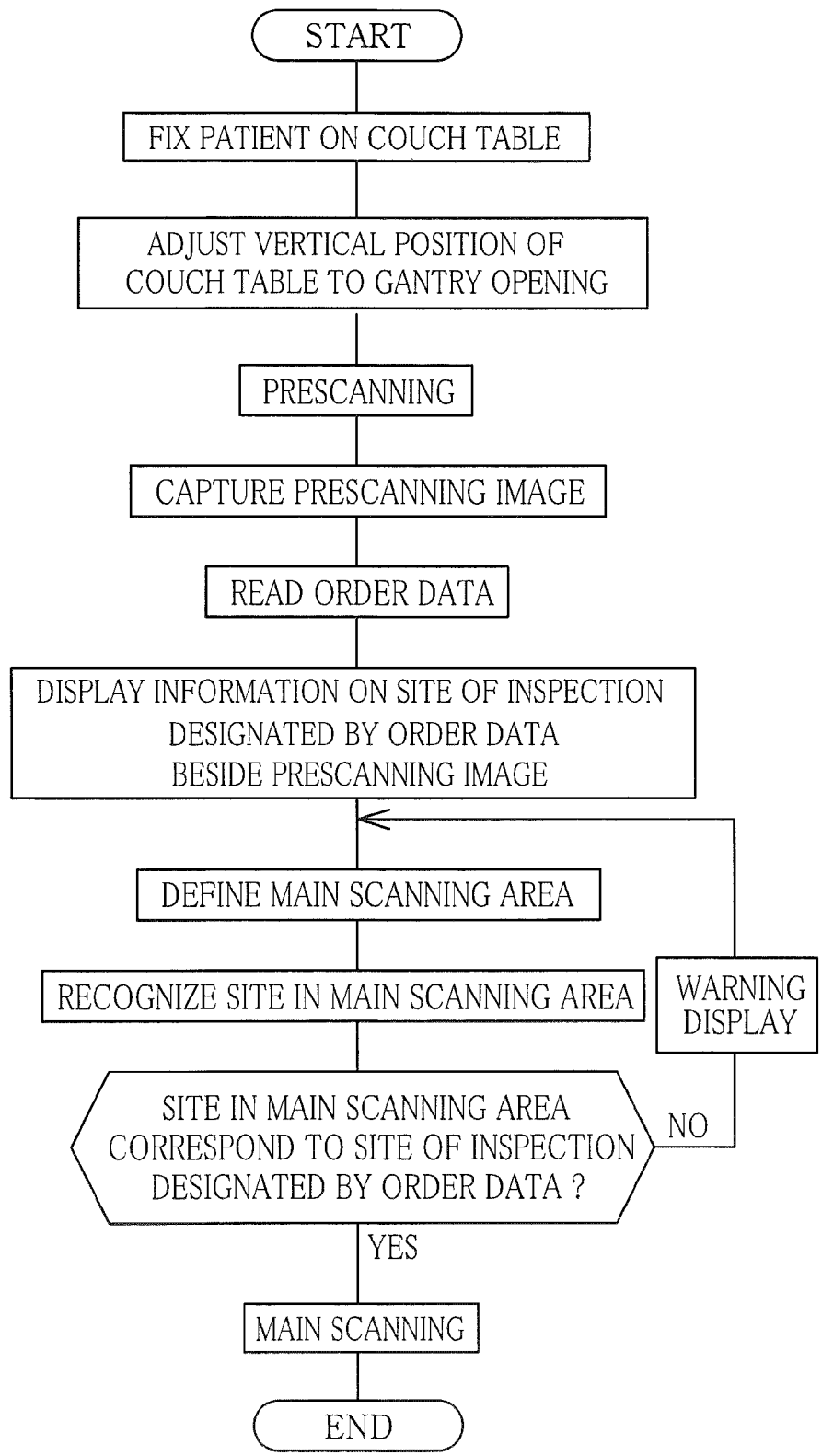
FIG. 11 is a flow chart illustrating a fifth sequence for capturing images of a patient, wherein information on a site of inspection is displayed beside a prescanning image, and judgment is done as to whether a main scanning area defined by an operator corresponds to the order data or not.

FIG. 11 shows a fourth embodiment of the present invention. As shown in the flow chart of FIG. 11, corresponding order data is read out from an HDD 62 immediately after a prescanning image PI is captured. Then, the captured prescanning image PI is displayed with start and end lines 82 and 84 on a control screen 80, and a window 90 is popped up beside the prescanning image PI to display information on the site of inspection designated by the order data. Thereby, the operator can pay attention to which site of inspection while defining a main scanning area by shifting the lines 82 and 84 on the prescanning image PI.

When the operator completes defining the main scanning area, a CPU 60 sends data of the prescanning image PI and setup data of the main scanning area to a site recognizer 70, and gets a site recognition result. Then, the CPU 60 judges based on corresponding order data and the site recognition result if the site in the defined main scanning area corresponds to the site of inspection designated by the order data. If the site in the main scanning area corresponds to the site designated by the order data, the CPU 60 starts main scanning. If not, the CPU 60 displays a warning in the same way as shown in FIG. 6.

Figure 5:
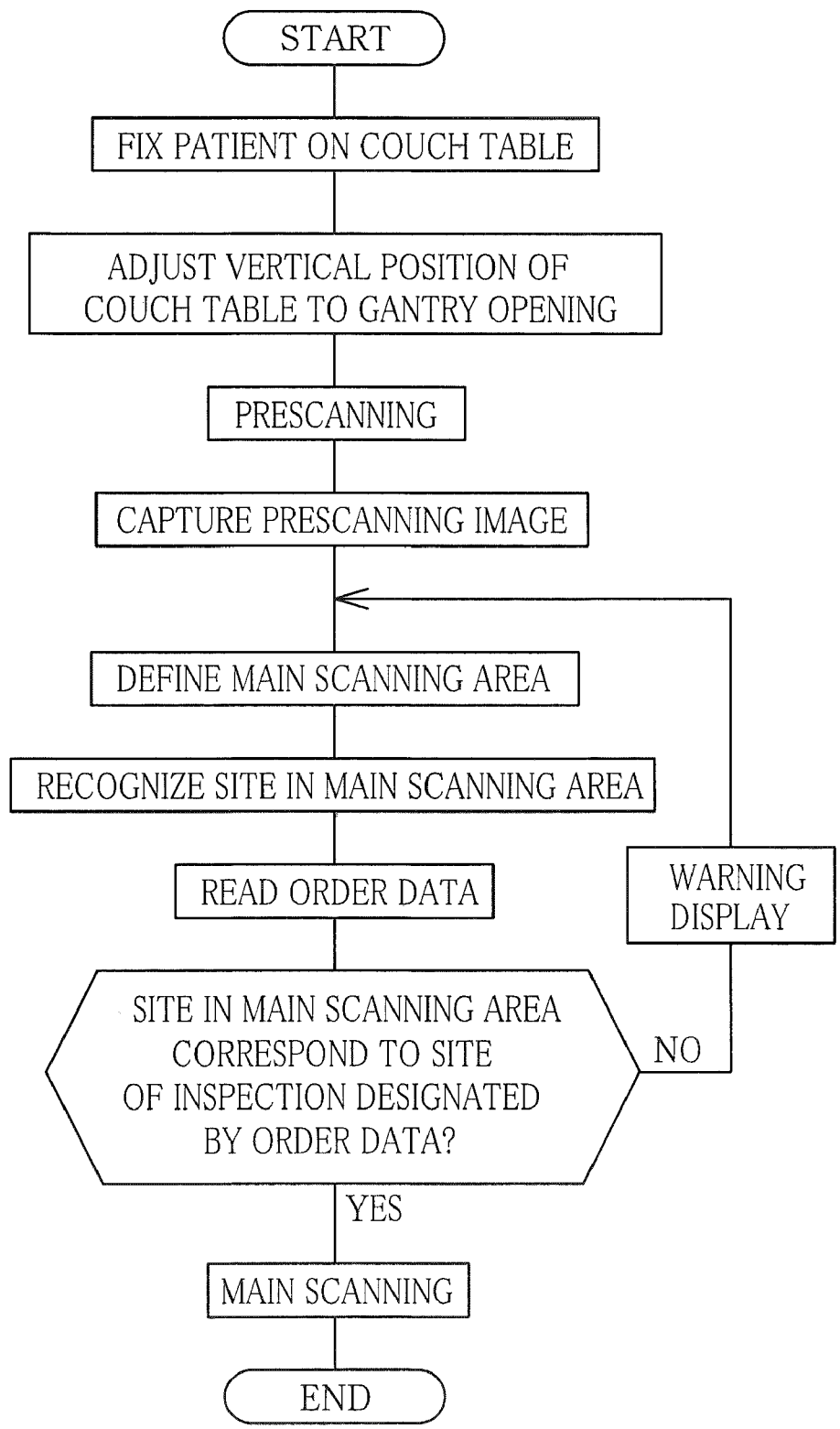
FIG. 5 is a flow chart illustrating a sequence for capturing images of a patient by the CT scanner, wherein judgment is done as to whether a main scanning area defined by an operator corresponds to order data or not.

In the embodiment shown in FIG. 9, the site recognition is carried out after the main scanning area is defined, so as to recognize the site located in the main scanning area, like in the embodiment shown in FIG. 5. It is alternatively possible to recognize the sites contained in the prescanning image PI before the main scanning area is defined, like in the embodiment shown in FIG. 7. It is also possible to define the main scanning area automatically with reference to the order data and display the lines 82 and 84 to show the automatically defined main scanning area as default positions, like in the embodiment shown in FIG. 9.

Figure 12:
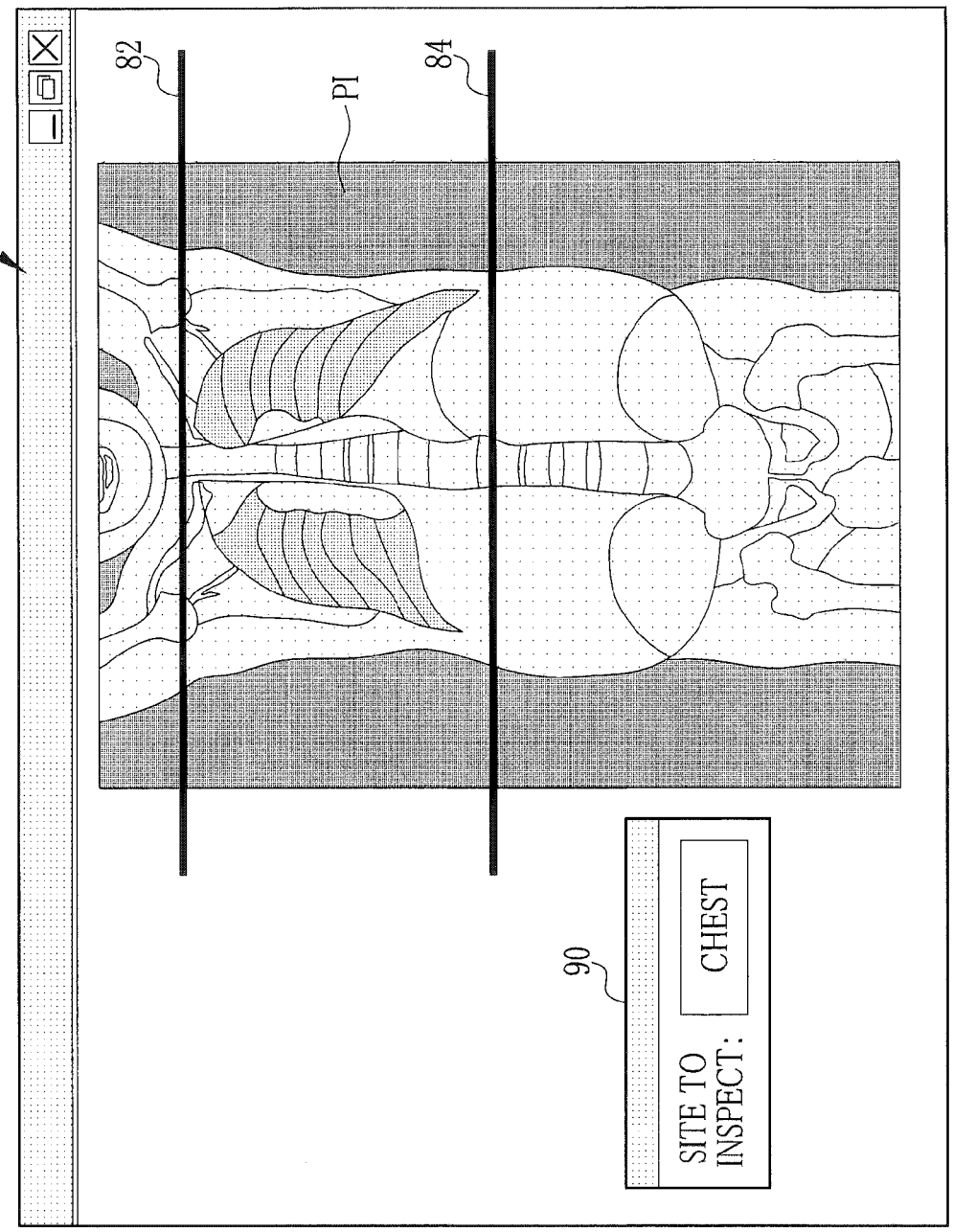
FIG. 12 is an explanatory diagram illustrating an example of a control screen displaying the information on the site of inspection beside the prescanning image.

Although the embodiment shown in FIG. 12 displays the information on the site of inspection in the popup window 90 beside the prescanning image PI, it is possible to display other kinds of information, such as the slicing thickness, together with the site of inspection. It is not always necessary to display the information and the prescanning image side by side, but it is also possible to display the information in place of the prescanning image by switching the windows on the control screen 80.

Figure 13:
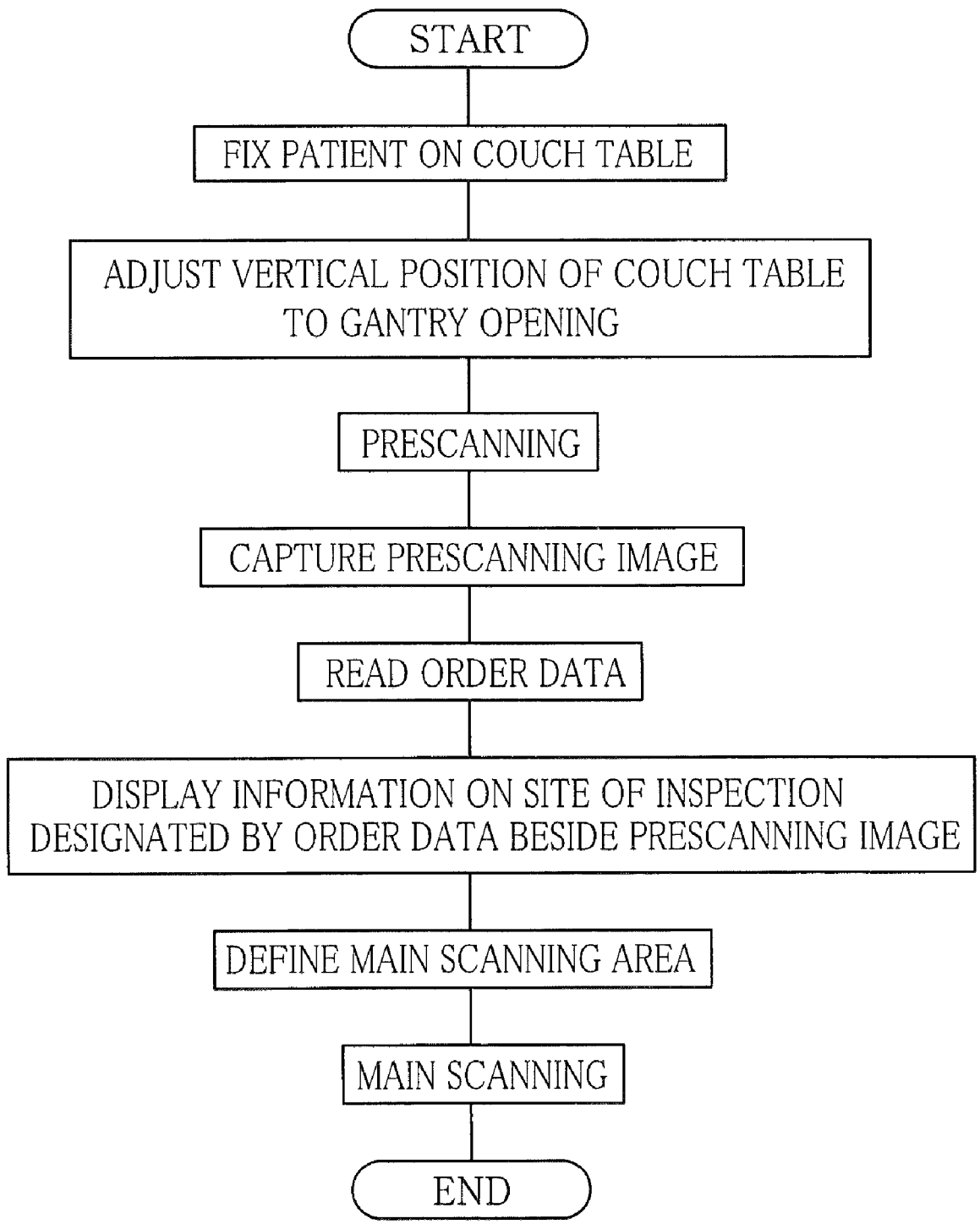
FIG. 13 is a flow chart illustrating a sixth sequence for capturing images of a patient, wherein information on a site of inspection is displayed beside a prescanning image, and main scanning is carried out without judgment as to whether a main scanning area defined by an operator corresponds to the order data or not.

In the embodiment shown in FIG. 11, judgment as to whether the site located in the main scanning area corresponds to the site designated by the order data or not is carried out after the main scanning area is defined by the operator. However, displaying the information on the site of inspection beside the prescanning image PI will prompt the operator to be careful enough about defining the main scanning range. So it is possible to omit the judgment process, and just display the information on the site of inspection beside the prescanning image PI, as shown in the flow chart of FIG. 13.

Although the above-described embodiments capture a perspective image from one direction of the patient as the prescanning image PI, the present invention is not limited to these embodiments, but another kind of image is usable as the prescanning image. For example, the prescanning image may be a tomographic image taken vertically to a body axis, called an axial image, or a tomographic image of another plane that is reconstructed from the axial image through Multi Planer Reconstruction (MPR) process. In that case, the prescanning may be done by capturing several axial images within a predetermined prescanning area, or a couple of axial images at a start point and an end point of the prescanning area, or a single axial image at the start point or the end point.

The above embodiments display the warning popup window 86 on the control screen 80 of the monitor 44 when the site located in the main scanning area does not correspond to the site of inspection. But the warning may be given other ways, for example, by lightening a specific lamp, or by ringing an alarm. It is possible to display the popup window 90 of the information on the site of inspection simultaneously with the warning.

Although body sites, such as head, chest, abdomen, pelvic region and limbs, are referred to as the anatomical structures to be recognized by the site recognizer 70 in the above embodiments, other anatomical structures, such as brain, heart, lungs, liver, stomach and other organs, may be recognized by the site recognizer 70.

Although the CT scanner 12 is referred to as the modality in the above embodiments, the present invention is not limited to these embodiments, but applicable to any kinds of modalities such as a MRI scanner, which carry out prescanning and main scanning to capture images for medical application.

Thus the present invention is not to be limited to the above embodiments but, on the contrary, various modifications will be possible without departing from the scope of claims appended hereto.

What is claimed is:

1. An imaging method for capturing images for medical application, comprising steps of:
   inputting order data designating an anatomical structure as an object of inspection;
   prescanning a patient to take at least a prescanning image;
   defining with reference to the prescanning image a main scanning area in which images for medical application are to be captured;

recognizing anatomical structures contained in the prescanning image by analyzing the prescanning image;
judging on the basis of the order data and results of said recognizing step whether the defined main scanning area corresponds to the anatomical structure designated by the order data; and
warning when the defined main scanning area does not correspond to the anatomical structure designated by the order data.

2. An imaging method as recited in claim 1, wherein said recognizing step is executed after said defining step, to recognize merely those anatomical structures which are located in the defined main scanning area.

3. An imaging method as recited in claim 1, wherein said recognizing step is executed before said defining step, to recognize all anatomical structures contained in the prescanning image.

4. An imaging method as recited in claim 3, wherein an area corresponding to the anatomical structure designated by the order data is defined to be the main scanning area in said defining step on the basis of the order data and recognition results of said recognizing step.

5. An imaging method as recited in claim 4, wherein said defining step includes steps of displaying the prescanning image with the defined main scanning area on a screen and, when necessary, correcting the main scanning area on the screen.

6. An imaging method as recited in claim 1, wherein said defining step includes steps of displaying the prescanning image on a screen, and defining the main scanning area on the displayed prescanning image.

7. An imaging method as recited in claim 6, wherein said defining step further includes step of displaying information on the anatomical structure designated by the order data.

8. An imaging method as recited in claim 1, wherein said prescanning step includes steps of radiating rays from one direction to the patient, detecting rays transmitted through the patient, and obtaining a perspective image of the patient as the prescanning image based on the detected rays.

9. An imaging method as recited in claim 1, wherein the anatomical structures includes body sites such as head, chest, abdomen, pelvic region and limbs, and organs such as brain, heart, lung, liver and stomach.

10. An imaging method for capturing images for medical application, comprising steps of:
inputting order data designating an anatomical structure as an object of inspection;
prescanning a patient to take at least a prescanning image;
recognizing, via a site recognizor implemented by a processor, anatomical structures contained in the prescanning image by analyzing the prescanning image by calculating characteristic amounts of the prescanning image based on computed tomography (CT) values of individual pixels of the prescanning image;
defining an area corresponding to the anatomical structure designated by the order data to be a main scanning area on the basis of the order data and recognition results of said recognizing step; and
scanning across the main scanning area, to capture images for medical application from the designated anatomical structure,
wherein the recognizing further comprises comparing the calculated characteristic amounts with previously stored characteristic amounts of respective body sites.

11. An imaging method as recited in claim 10, wherein said defining step includes steps of displaying the prescanning image with the defined main scanning area on a screen and, when necessary, correcting the main scanning area on the screen.

12. An imaging method as recited in claim 11, further comprising steps of:
judging on the basis of the order data and the recognition results of said recognizing step whether the corrected main scanning area corresponds to the anatomical structure designated by the order data; and
warning when the corrected main scanning area does not correspond to the anatomical structure designated by the order data.

13. An imaging method as recited in claim 10, wherein the recognizing step is performed automatically.

14. An imaging method as recited in claim 10, wherein the recognizing is performed without operator intervention.

15. An imaging method for capturing images for medical application, comprising steps of:
inputting order data designating an anatomical structure as an object of inspection;
prescanning a patient to take at least a prescanning image;
recognizing, via a site recognizor implemented by a processor, anatomical structures contained in the prescanning image by analyzing the prescanning image by calculating characteristic amounts of the prescanning image based on computed tomography (CT) values of individual pixels of the prescanning image;
displaying information on the anatomical structure designated by the order data and the prescanning image on a screen; and
defining a main scanning area, in which images for medical application are to be captured, with reference to the displayed prescanning image and the information on the designated anatomical structure,
wherein the recognizing further comprises comparing the calculated characteristic amounts with previously stored characteristic amounts of respective body sites.

16. An imaging method as recited in claim 15, wherein the recognizing is performed automatically.

17. An imaging method as recited in claim 15, wherein the recognizing is performed without operator intervention.

18. A modality for capturing images for medical application comprising:
a device for inputting order data designating an anatomical structure as an object of inspection;
a device for prescanning a patient to take at least a prescanning image;
a device for defining with reference to the prescanning image a main scanning area in which images for medical application are to be captured;
a device for recognizing anatomical structures contained in the prescanning image by analyzing the prescanning image;
a device for judging on the basis of the order data and recognition results of said recognizing device whether the defined main scanning area corresponds to the anatomical structure designated by the order data; and
a device for warning when the defined main scanning area does not correspond to the anatomical structure designated by the order data.

* * * * *